(12) United States Patent
Landau

(10) Patent No.: US 6,264,629 B1
(45) Date of Patent: *Jul. 24, 2001

(54) SINGLE-USE NEEDLE-LESS HYPODERMIC JET INJECTION APPARATUS AND METHOD

(75) Inventor: Sergio Landau, Laguna Niguel, CA (US)

(73) Assignee: Bioject, Inc., Portland, OR (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/252,131

(22) Filed: Feb. 18, 1999

Related U.S. Application Data

(63) Continuation-in-part of application No. 09/195,334, filed on Nov. 18, 1998, now Pat. No. 6,096,002.

(51) Int. Cl.[7] .............................. A61M 5/30; A61M 37/00
(52) U.S. Cl. ................................ 604/68; 604/69; 604/143
(58) Field of Search ............................... 604/68–72, 140, 604/141, 143, 148, 232, 131

(56) References Cited

U.S. PATENT DOCUMENTS

| | | |
|---|---|---|
| 3,688,765 * | 9/1972 | Gasaway ........................ 128/173 H |
| 4,266,541 | 5/1981 | Landau . |
| 4,592,742 | 6/1986 | Landau . |
| 4,596,556 * | 6/1986 | Morrow et al. ...................... 604/70 |
| 4,652,261 * | 3/1987 | Mech et al. ........................ 604/130 |
| 4,790,824 * | 12/1988 | Morrow et al. ..................... 604/143 |
| 5,080,648 | 1/1992 | D'Antonio . |
| 5,318,522 | 6/1994 | D'Antonio . |
| 5,569,190 | 10/1996 | D'Antonio . |
| 5,921,967 * | 7/1999 | Sadowski et al. .................. 604/218 |

OTHER PUBLICATIONS

Vitajet Industria e Comércia Ltda. Ommijet sales brochure, 4 pp, Rio de Janeiro, Brazil, undated.

* cited by examiner

*Primary Examiner*—Richard K. Seidel
*Assistant Examiner*—Michael Hayes
(74) *Attorney, Agent, or Firm*—Terry L. Miller

(57) ABSTRACT

A gas-powered, single-use, needle-less hypodermic jet injection device includes a hand-held injector, and a drug injection cartridge which provides a cylinder of liquid medication to be injected, an injection orifice, and an injection piston. Forceful movement of the injection piston in the cylinder causes an injection jet of medication to be expelled from the injection orifice. The injection device also includes a hermetically sealed gas pressure capsule which remains sealed until the moment of injection and powers the jet injection after opening of this cartridge.

20 Claims, 4 Drawing Sheets

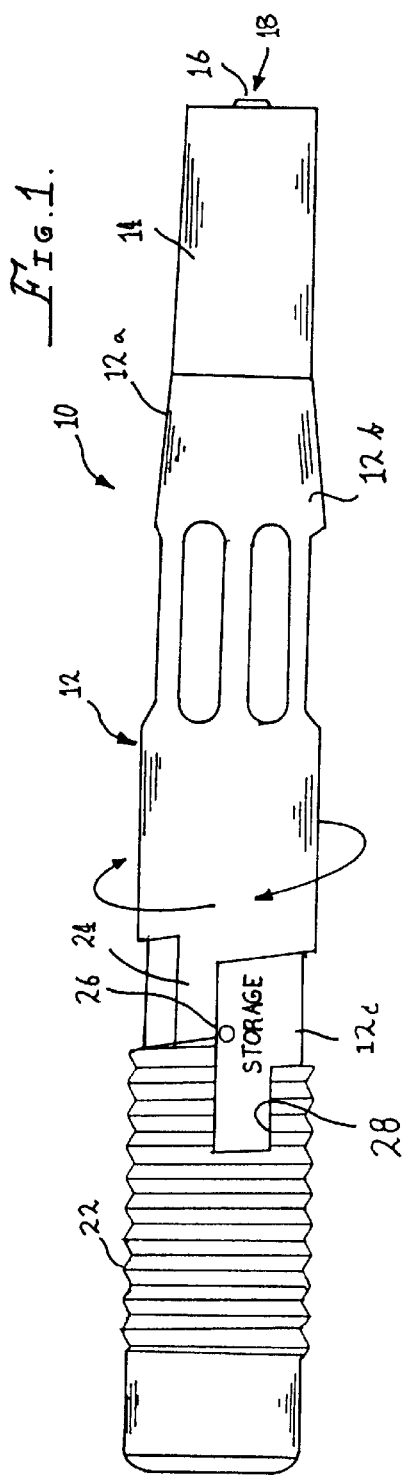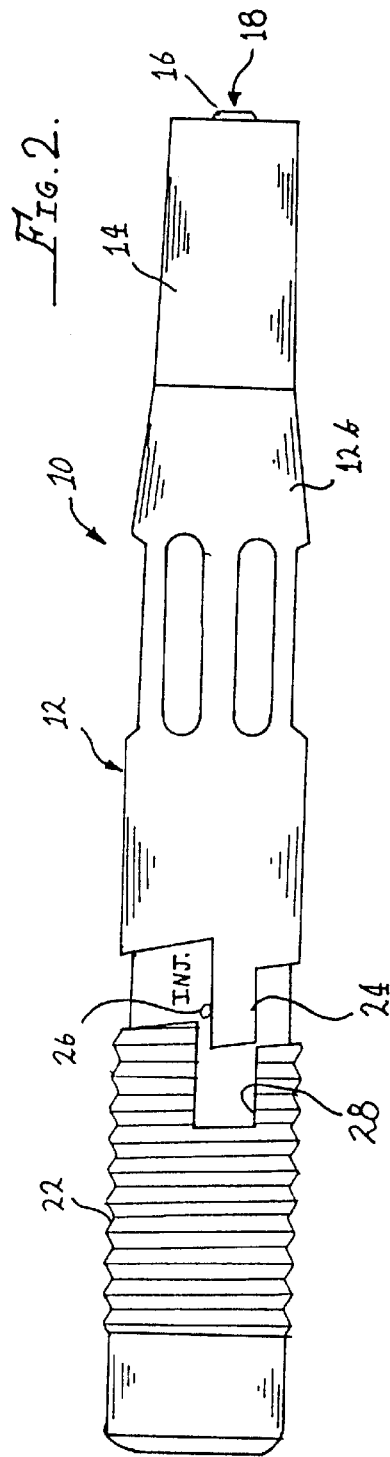

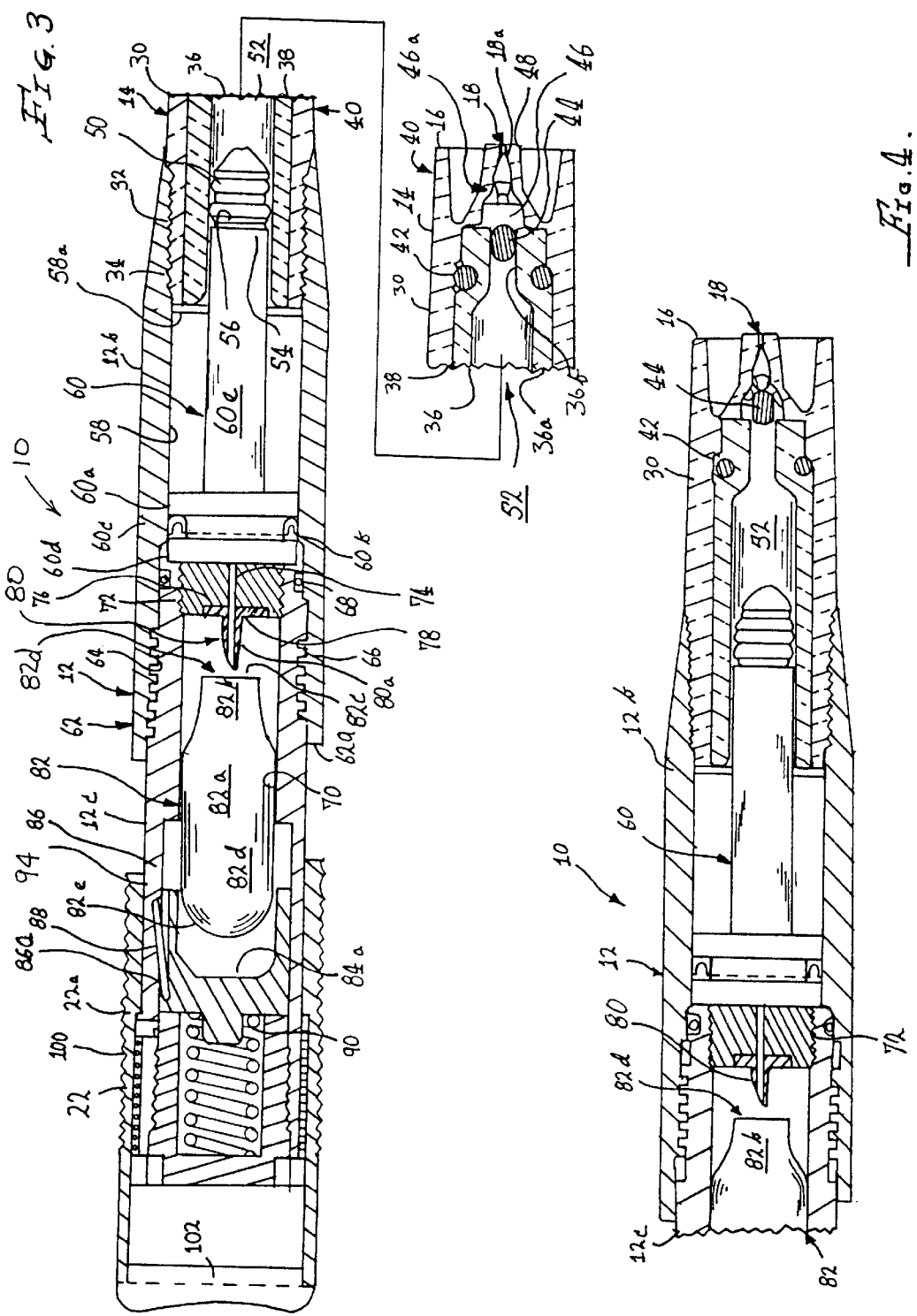

SINGLE-USE NEEDLE-LESS HYPODERMIC JET INJECTION APPARATUS AND METHOD

CROSS REFERENCE TO RELATED APPLICATION

This application is a Continuation-in-Part of U.S. patent application Ser. No. 09/195,334, filed Nov. 18, 1998, now U.S. Pat. No. 6,096,002.

BACKGROUND OF THE INVENTION

1. Field of the Invention

The present invention relates generally to a single-use disposable needle-less (or needle-free) hypodermic jet injection device. Particularly, this invention relates to such a jet injection device which comprises a hand-held injector having a pre-filled drug cartridge sealingly carrying injectable medication, a sealed cylinder of pressurized gas, a pre-energized discharge mechanism for penetrating the gas cylinder, and a trigger device for releasing the discharge mechanism. Features are provided which simultaneously unseal the drug cartridge and prepare the device for performing a jet injection when a user of the device changes it from a storage configuration to a use configuration. When the user actuated the injection device, the trigger device releases the discharge mechanism to penetrate the gas cylinder, which drives a piston of the drug cartridge to effect a hypodermic jet injection.

2. Related Technology

Needle-less or needle-free hypodermic jet injection devices have been in commercial use for over 40 years. A number of these devices have used pressurized gas to power a hypodermic jet injection. The related technology includes a number of teachings for gas-powered injection devices, including: U.S. Pat. No. 4,596,556, issued Jun. 24, 1986 to J. Thomas Morrow, et al.; U.S. Pat. No. 4,913,699; issued Apr. 3, 1990 to James S. Parsons; and U.S. Pat. No. 5,730,723, issued Mar. 24, 1998, to Thomas P. Castellano, et al. WIPO publication WO 97/37705 also discloses a gas powered disposable needle-less hypodermic jet injector.

The Morrow, et. al. '556 patent is believed to teach a reusable hypodermic jet injection device in which a housing receives a shell or cartridge having a bore leading to a discharge aperture. Within the bore is received both a plunger sealingly engaging the bore, and a pressurized gas cylinder which rests against the plunger. The injection device includes a ram which has a penetrating tip confronting a penetrable wall section and seal of the gas cylinder, and a discharge mechanism for driving the ram through the penetrable wall section of the gas cylinder when a trigger device is released. Discharge of the pressurized gas from the cylinder drives the plunger to effect a jet injection, and also drives the seal of the gas cylinder to effect resetting of the discharge mechanism. The shell with its plunger, and spent gas cylinder, is discarded after an injection; and a new shell pre-filled with medication and with a new gas cylinder is used for each injection.

The Parsons '699 patent is believed to teach a single-use jet injector which is totally discarded after one use. This injector is believed to have a body with a pair of gas chambers separated by a breakable valve. One of the gas chambers contains a pressurized gas, while the other chamber is sealingly bounded by a piston which drives a plunger. The plunger sealingly bounds a chamber into which a dose of medication is loaded by the user before the injection. This medication dose chamber leads to an injection orifice so that when the valve is broken, the piston and plunger are moved by pressurized gas communicated to the second chamber, and the plunger drives the medication forcefully out of the injection orifice to form an injection jet. After a single use, the device is discarded.

The Castellano '723 patent, which was issued in 1998 and which does not cite the earlier Parsons '699 patent, is believed to teach substantially the same subject matter as Parsons et al.

WIPO publication WO 97/37705 published pursuant to a Patent Cooperation Treaty (PCT) application for joint inventors Terence Weston and Pixey Thornlea, is believed to disclose a disposable hypodermic jet injector in which the device is powered by a gas pressure spring of the type common in the tool and die art as a substitute for the conventional metal spring-powered ejector pin. In the Weston device, the ram of the gas pressure spring is held in a contracted position by a trigger mechanism. When the trigger mechanism is released, the gas pressure spring is supposed to expand and drive a piston sealingly received in a bore and leading to a fine-dimension orifice in order to produce a jet hypodermic injection from liquid held in the bore ahead of the piston.

The Weston device is thought to have several deficiencies: such as difficult and costly manufacturing and sterilization processes, because pressurized gas and a drug dose need to be contained in the same package; and including a possible inability to endure long-term storage while still retaining the gas pressure in the gas spring to power an injection, and also maintaining the medication integrity. In other words, the gas pressure spring of the Weston device contains only a small quantity of gas, and depends upon the sealing relationship of the ram of this spring with a cylinder within which the ram is movably and sealingly received in order to retain this gas pressure. Even a small amount of gas leakage over time will be enough to render this injector inoperative.

SUMMARY OF THE INVENTION

In view of the above, it is desirable and is an object for this invention to provide a needle-less hypodermic jet injection device which reduces the severity of or avoids one or more of the limitations of the conventional technology.

Thus, it is an object of this invention to provide a single-use, disposable, needle-free gas-powered hypodermic jet injector utilizing a pressurized gas source which is hermetically sealed until the moment of injection.

Further, an object of this invention is to provide such a gas powered jet injector in which the device has a storage configuration and a use configuration. In the storage configuration, the device is safe, with the drug cartridge sealed closed, and is incapable of effecting a jet injection. In the use configuration, the device is prepared for making a jet injection, with the drug cartridge opened in preparation for this injection.

Additionally, an object for this invention is to provide such an injection device having a multi-function component which alternatively maintains the injector in a safe storage condition, and also allows a user to place the injection device into a use condition preparatory for performing a jet injection. When the user placed the device into the use configuration, the multi-function component prepares the jet injection device by effecting unsealing of the previously sealed drug cartridge, and also removes a safety block from an obstructing position relative to a trigger of the device. Thereafter, the trigger of the injector can be manually activated by a user of the device to perform an injection.

Accordingly, a needle-less hypodermic jet injection system embodying this invention includes, for example: a hand piece assembly having a body including a drug injection cartridge with a medication cylinder pre-filled with substantially incompressible liquid medication such that substantially no ullage volume exists in said medication cylinder, said medication cylinder leading to an outlet orifice a plug-capture chamber and a drug injection nozzle, a sealing member sealingly and movably received in said outlet orifice, and a drug-injection piston; the hand piece assembly further defining a first bore within the body for movably receiving a gas-power piston, a gas power piston movably received in the first bore and having a ram portion extending into the drug injection cartridge to abut with the drug-injection piston, the body and gas-power piston cooperating to define a first variable-volume chamber in the first bore; the body also defining an elongate second bore in gas communication with the first bore and separated therefrom by a center wall portion of the body, a cylindrical gas capsule received into the second bore, the gas capsule having a penetrable wall section disposed toward the center wall, the center wall carrying a penetrator disposed toward the penetrable wall section of the gas capsule, and the hand piece assembly carrying a discharge mechanism including a trigger member outwardly disposed on the body and a hammer movable in the body in response to actuation of the trigger to forcefully move the gas capsule in the second bore so as to impale the gas capsule at the penetrable wall section thereof upon the penetrator and thus to communicate pressurized gas to the first chamber; whereby, the pressurized gas in the first chamber drives the gas-power piston to effect a hypodermic jet injection from the drug injection cartridge, and the body and trigger member cooperatively defining a first relative position in which said ram portion confronts but does not displace said injection piston so that said sealing member is disposed in said outlet orifice to maintain said drug injection cartridge sealingly closed, and said body and trigger member in a second relative position preparatory to effecting a jet injection causing said ram portion to abut and move said drug injection piston to a second position displacing said drug injection piston to a second position so that said sealing member is displaced from said outlet orifice into said plug-capture chamber by said liquid medication and unseals said drug injection cartridge.

Additional objects and advantages of this invention will appear from a reading of the following detailed description of a single exemplary preferred embodiment, taken in conjunction with the appended drawing Figures, in which the same reference numeral is used throughout the several views to indicate the same feature, or features which are analogous in structure or function.

BRIEF DESCRIPTION OF THE DRAWING FIGURES

FIG. 1 provides an exterior side elevation view of a single-use, needle-less hypodermic jet injector device embodying the present invention, and in which the device is in a "storage" configuration;

FIG. 2 is an exterior side elevation view of the injector device seen in FIG. 1, but with the device shown in an "inject" configuration preparatory to effecting a hypodermic jet injection;

FIG. 3 provides a longitudinal cross sectional view through the needle-less hypodermic jet injection device of FIG. 1, and shows the device in the "storage" configuration;

FIG. 4 is a fragmentary cross sectional view similar to FIG. 3, but shows the hypodermic jet injection device in the "inject" configuration;

FIG. 5 is also a fragmentary cross sectional similar to FIGS. 3 and 4, but shows the hypodermic jet injection device during the process of effecting a jet injection;

FIG. 6 is a fragmentary cross sectional view similar to a portion of FIG. 4, but shows a respective portion of an alternative embodiment of a single-use, needle-less hypodermic jet injection device according to the present invention;

Figure 7:
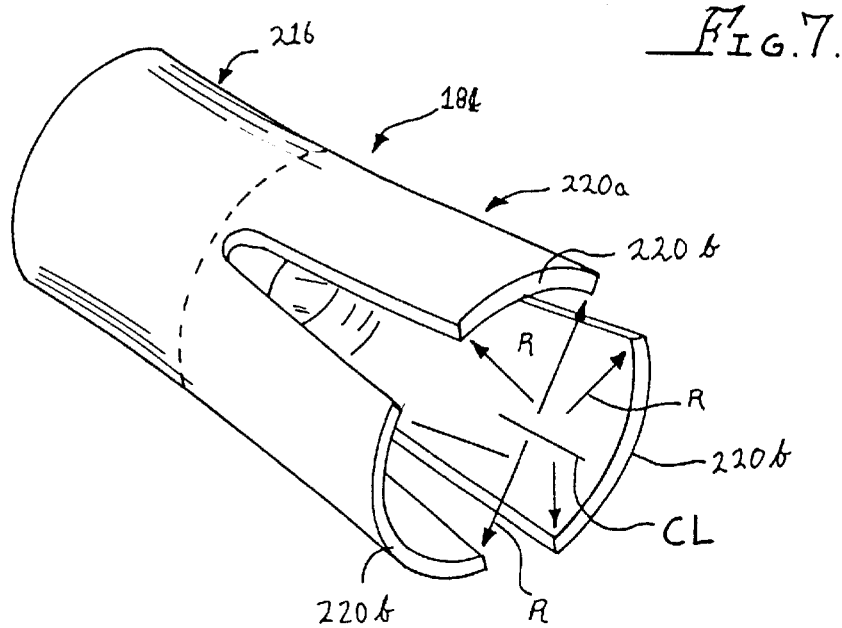
FIG. 7 is a perspective view of a portion of the device seen in FIG. 6.
Figure 8:
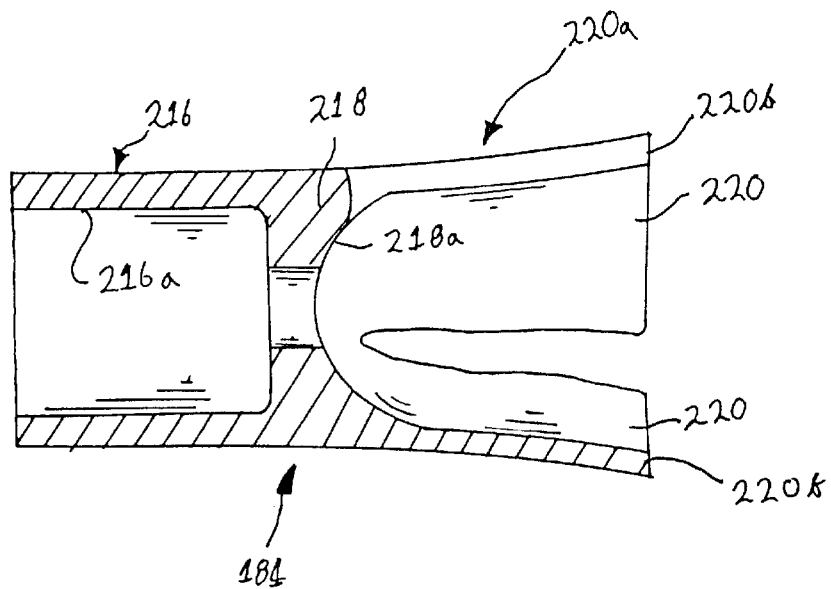

FIG. 8 provides a cross sectional view of the portion of the device seen in FIG. 7.

DETAILED DESCRIPTION OF EXEMPLARY PREFERRED EMBODIMENTS OF THE INVENTION

Overview, Storage of the Device, and its Preparation for Effecting a Jet Injection Viewing FIG. 1, a needle-free, hypodermic jet injection device 10 is shown in a storage configuration in which it is maintained until it is prepared for its use in administering an injection. In this storage configuration, the device is incapable of effecting a jet injection, is safe, and can be stored for a comparatively long time while requiring only a moment of preparation before it can be used to make a jet injection of the medication within the device 10.

The device 10 includes a hand piece assembly 12, preferably fabricated principally of injection molded plastic polymers, and with a body 12a including a pre-filled drug injection cartridge or medication cylinder 14. The word "drug" as used herein is intended to encompass, for example, and without limitation, any medication, pharmaceutical, therapeutic, vaccine, or other material which can be administered by jet injection. Essentially, such an injectable medication is in the form of a substantially incompressible liquid, and as will be seen, this liquid substantially fills the drug injection cartridge so that no ullage volume of compressible gas is present in this cartridge.

The pre-filled drug injection cartridge 14 has an end surface 16 at which is defined a fine-dimension injection orifice or injection nozzle opening 18. When the device 10 is used to effect an injection, a high velocity jet of liquid medication issues from this orifice (as is indicated by arrow 20 of FIG. 5). To use the device 10, it is first placed in an "inject" configuration, the end surface 16 is pressed against the skin of a patient who is to receive the jet injection, and then the device 10 is triggered so that the jet 20 issues out and penetrates the skin. Thus, the liquid medication enters the tissues of the patient without the use of a hypodermic needle.

Placing the device 10 in the "inject" configuration is effected manually by a user of the device 10 who rotates a first portion 12b of the body 12a relative to a second portion 12c. As is seen in FIG. 1, the body portion 12c carries a trigger sleeve 22, while the portion 12b carries a projection 24 abutting this sleeve. The projection 24 and a blocking pin 26 cooperate to prevent the body portions 12b and 12c from being relatively rotated except in the direction of the arrow of FIG. 1. When a user effects this relative rotation of the body portions 12b and 12c through a rotation of almost 360°, then this relative rotation aligns the projection 24 with a recess 28 on the trigger sleeve 22, reveals the abbreviation of the word "inject" (indicated on FIG. 2 by the letters "INJ") on the body portion 12c.

This relative rotation of the body portions 12b and 12c also effects a selected relative axial movement of these body portions toward one another (as will be further described below), and places the device 10 in the "inject" configuration seen in FIG. 2. In this "inject" configuration, the device 10 is positioned with its surface 16 against the skin of the person who is to receive the injection, and an axial pressure is applied to the trigger sleeve 22. The trigger sleeve 22 moves axially along the body portion 12c, and this movement triggers the device 10 to effect injection jet 20 (recalling FIG. 5).

Structure of the Device 10

Figures 5, 6:
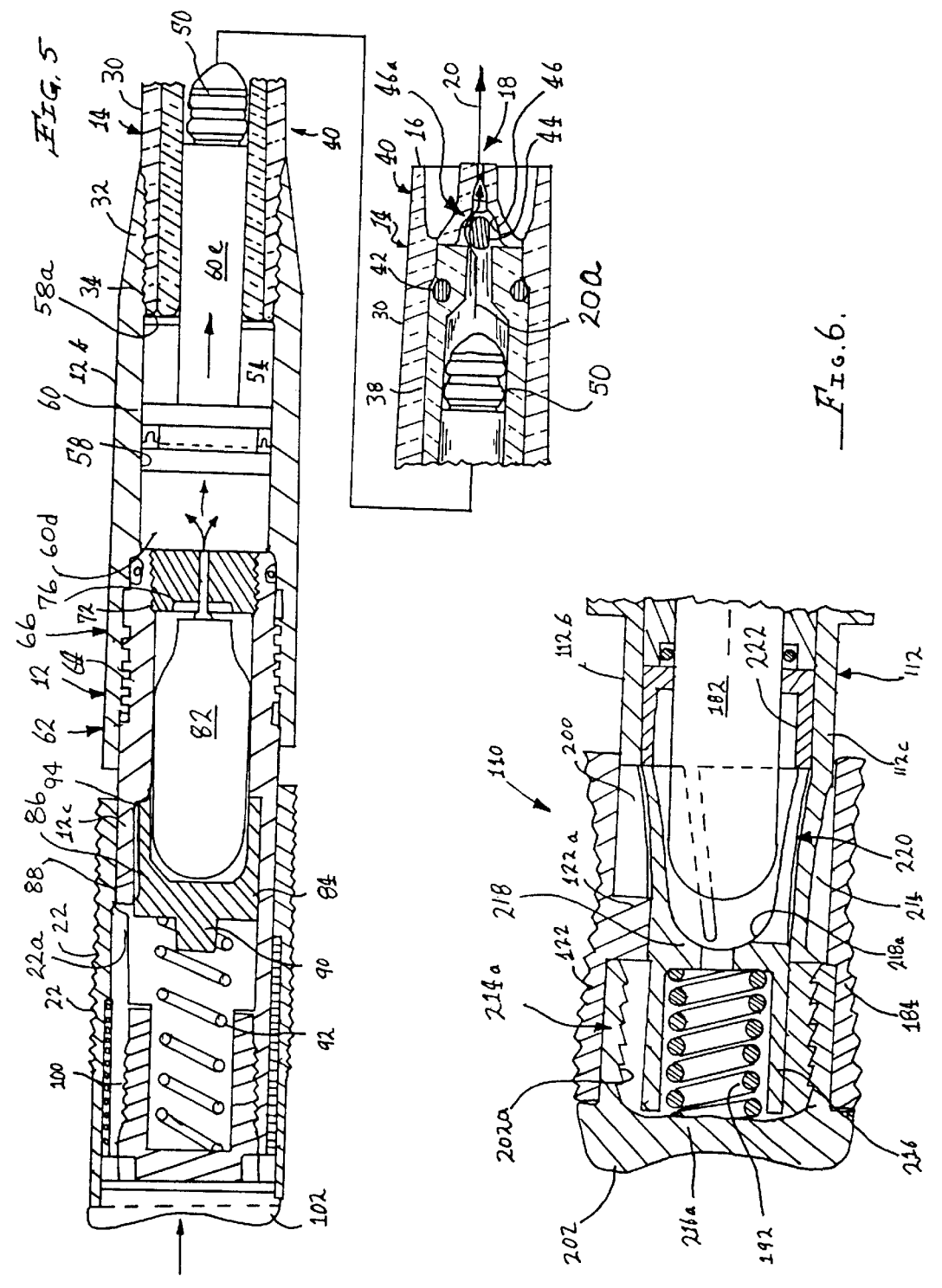

Turning now to FIGS. 3, 4, and 5, in conjunction with one another, FIG. 3 shows the device 10 in the storage configuration of FIG. 1 preparatory to giving an injection. In FIG. 4 shows the device in the "inject" configuration, and FIG. 5 shows the device during the brief interval of an injection. In these Figures, it is seen that the drug cartridge 14 includes a cylindrical body 30 defining an external thread section 32. This external thread 32 is threadably received by a matching internal thread section 34 of the body portion 12b. Preferably, a thread locking compound, such as an anaerobic adhesive, is applied to the threads 32 of the cartridge 14 when it is assembled to the body portion 12b during manufacture of the device 10. Alternatively, a self-locking thread design or a thread-locking feature may be used on the device 10 to prevent the drug injection cartridge 14 from being removed from the device 10. Thus, the cartridge is not removable from the device 10, and the device 10 and cartridge 14 are disposed of after the first and only injection effected with the device 10.

An advantageous feature of the device 10 embodying the present invention, and one which results from this construction of the device, is that the injection cartridge 14 may be manufactured and filled at a drug company (without the drug manufacture having to be concerned with handling capsules of pressurized gas), the gas pressure capsule of the device may be manufactured and filled at a factory devoted to this item (without this manufacturer having to handle drugs), and the hand piece assembly of the device may be manufactured at yet another location, if desired. Subsequently, completion of the device 10 requires merely the combining of the hand piece assembly, gas capsule, and drug injection cartridge.

The body 30 of cartridge 14 defines a stepped through bore 36 having a larger diameter portion 36a which extends substantially the length of the body 26. Adjacent to the forward end of the body 30 (i.e., adjacent to the end defining surface 16), the bore 36 steps down and defines an outlet orifice 36b. It is seen that the bore portion 36a and outlet orifice 36b are defined by a glass sleeve 38 which is received into a molded plastic body 40. An O-ring type of seal member 42 prevents leakage between the glass sleeve 38 and the body 40.

As those who are ordinarily skilled in the pertinent arts will understand, many medications are not suitable for long-term storage in contact with plastics, but will store satisfactorily in contact with glass. Thus, this construction of the cartridge 14 makes it suitable for long-term storage of even medications of this nature. However, for medications that will store satisfactorily in contact with plastic polymers, this construction detail is optional and the entire injection cartridge body 30 may be formed of a selected polymer.

In the embodiment of cartridge 14 having the glass sleeve 38, the outlet orifice 36b is sealingly closed in the storage configuration of the device 10 by a plug 44. Importantly, viewing FIGS. 3–5, it is seen that the cartridge 14 defines a plug-capture chamber 46 immediately outside of the outlet orifice 36b (i.e., rightwardly of this outlet orifice, viewing FIGS. 3–5). The plug capture chamber 46 includes a radial array 46a of individual radially inwardly and axially extending ribs 48 disposed in a spaced relation to the outlet orifice 36b. These ribs 48 are arrayed radially about and in a transition bore portion 18a leading to the injection orifice 18. Thus, as will be seen, the plug member 44 can be received into the plug-capture chamber 46 and be supported on the ribs 48 without it blocking the injection orifice 18.

Sealingly and movably received in the bore section 36a is a resilient piston member 50. This piston member defines multiple circumferential grooves 50a interdigitated with sealing ribs 50b. The sealing ribs 50b sealingly and movingly engages the bore 36a of the injection cartridge (i.e., with the bore 36a of glass sleeve 38 in this case). The piston member 50 and body 30 cooperatively define a medication chamber 52 communicating outwardly of the cartridge 14 via the injection orifice 18. Prior to its use to effect an injection, the orifice 18 of each fresh and pre-filled device 10 will ordinarily also be sealed by an adhesively-applied, peel-off type of sealing membrane, which may be formed, for example, of foil or of a polymer/paper laminate. Such peel-off seals are conventional and well known, and for this reason, the seal formerly on cartridge 14 of device 10 as seen in FIG. 3 is not shown in the drawing Figures.

Further considering the cartridge 14, it is seen that the piston member 50 defines an abutment surface 54 confronting the opening of bore 36 on body 30. This surface 54 is abutted by an end surface 56 on an injection ram of the hand piece assembly 12 (which injection ram will be further described below). In the storage configuration of the device 10, the end surface 56 confronts piston member 50, but does not displace it from the position seen in FIG. 3. In this storage configuration of the device 10, the chamber 52 is sealed and is substantially full of incompressible liquid, without any substantial ullage volume of compressible gas being in the chamber 52. The injection ram will be understood as effective during a jet injection to forcefully move the piston member 50 inwardly of the bore section 36a toward the outlet orifice 36b.

Hand Piece Assembly 12

Considering now the hand piece assembly 12 in greater detail, as seen in FIGS. 1–5, it is seen that the body 12a generally is formed of two main cooperative tubular sections 12b and 12c, which are threadably engaged with one another to form the hand piece assembly 12. Preferably both of the body sections 12b and 12c, as well as other components of the device 12 not otherwise identified as being made of some other material, are all formed of plastic polymers. Further, the preferred process for making the device 10 is by injection molding of the components formed of plastic polymer, so that manufacturing costs are very low. Materials utilization for the device 10 is very small as well, so that disposing of the device after a single injection does not cause a serious environmental concern.

The forward tubular body section 12b defines a stepped through bore 58, a forward portion 58a of which opens at 58b forwardly on the body 12, and which inwardly of this bore opening 58a defines the internal thread section 34 for threadably receiving the external threads 32 on the drug cartridge 14. Sealingly and movably received in the bore portion 58a is a stepped injection piston member 60. A larger diameter portion 60a of this piston member defines a groove 60b carrying a seal member 60c. The seal member 60c movingly engages sealingly with the bore portion 58a and bounds a gas pressure chamber 60d, which is to the left of this piston member as seen in FIGS. 3, 4, and 5. It is to be noted that in FIGS. 3 and 4, this chamber 60d is at a minimal volume, and so the lead line from reference numeral 60d extends into the interface of the piston member 60 with the housing portion 12c.

A smaller diameter portion 60e of the piston member 60 is elongate and extends in the bore 58 to also be received into the bore portion 36a of the drug cartridge 14, as is seen in FIG. 3 in the storage configuration of the device 10. The piston portion 60e defines the end surface 56 which confronts and abuts the surface 54 of the piston member 50 of an drug cartridge 14. Thus, the piston portion 60e provides the injection ram of the device 10.

Considering the forward body section 12b in still greater detail, it is seen that this body section defines a tubular aft body section 62. This aft body section includes an axially disposed end surface 62a at which the stepped through bore 58 opens, and which defines an internal thread section 64 threadably engaging onto matching threads 66 of body section 12c. For purposes of explanation, and without limitation of the present invention, the threads 64 and 66 may have a pitch of about 14 threads per inch.

As is seen comparing FIGS. 1 and 2, the device 10 is converted from its storage to its "inject" configuration by rotating the body portions 12b and 12c in a relative rotational direction that threads these body portions together along threads 64 and 66. As was explained above, this relative rotation of the body sections 12b and 12c brings projection 24 into alignment with recess 28 on trigger sleeve 22, and makes possible the subsequent triggering of the device 10.

Still considering FIGS. 2 and 3, it is seen that the aft body portion 12c outwardly defines the thread section 66 and slidably carries the trigger sleeve 22. Adjacent to the thread section 66, the body portion 12c carries an O-ring type of sealing member 68 which sealingly engages the body portion 12b both when the body portions are in their "storage" relative configuration of FIG. 3, and also when these body portions are in their "inject" relative positions as is seen in FIGS. 4 and 5.

Body portion 12c defines a stepped through bore 70 which is substantially closed at the end of this bore adjacent to the forward body portion 12b by a wall member 72. This wall member 72 defines a stepped through bore 74 in a larger diameter part of which is seated a disk part 76 of a penetrator member 78. This penetrator member 78 includes a hollow penetrator spike 80 which itself has a bore 80a communicating through the wall member 72 via the smaller diameter portion of bore 74. Thus, the bore 70 is communicated to the chamber 60d adjacent to injection piston 60 in the body portion 12b.

Slidably received in the bore 74 adjacent to and confronting the penetrator member 78 is a gas pressure capsule 82. This gas pressure capsule 82 includes a body 82a, having a cylindrical outer wall portion 82a'. The capsule 82 is also necked down at a forward end to provide a reduced diameter portion 82b leading to an axially disposed end surface 82c defined by a penetrable wall section 82d (the wall section being indicated by the arrowed numeral in FIG. 3). The gas capsule 82 is preferably formed of metal, and contains a supply of pressurized gas. Because the pressurized gas is contained in the capsule 82 until the moment of injection, the plastic parts of the device 10 are not exposed to or stressed by this pressurized gas until an injection is effected using the device 10. For this reason, the device 10 is believed to have a much more reliable storage life then prior devices which attempt to contain pressurized gas in a plastic or plastic-composite containment.

The wall section 82d confronts and is spaced slightly from the penetrator spike 80. At an opposite or aft end of the capsule 82, this capsule defines an outwardly rounded end wall 82e.

Also slidably received into the bore 70 and confronting the end 82e of capsule 82 is tubular and cylindrical hammer member 84. This hammer member 84 defines an end surface 84a which is engageable with the surface 82e of capsule 82, an axially extending groove 86 having an end wall at 86a (into which a dowel pin 88 is received), and an axial protrusion at 90 which serves to center a spring 92.

The dowel pin 88 is engaged in a first position (i.e., in the "storage" configuration of the device 10) at end 86a of groove 86, and the other end of this pin rests upon a metal (i.e., preferably hardened steel) sear pin 94 carried by the body portion 12c. Thus, as is seen in FIGS. 3 and 4, the hammer 84 is maintained in a "cocked" position with the spring 92 pre-loaded between the hammer 84 and a spring seat member 96 threadably engaging into the end of body portion 12c.

In order to provide for movement of the trigger sleeve 22 to effect release of the hammer 84, the body portion 12c defines an axially extending slot 100, and the trigger sleeve 22 carries a radially inwardly extending trigger block 22a, which is slidably received in this slot 100 and which confronts the dowel pin 88, as is seen in FIG. 3. Also, an end cap 102 is adhesively retained onto the trigger sleeve 22 and closes the end of this trigger sleeve so that a user's thumb, for example, may be used to effect forward movement of the trigger sleeve when an injection is to be effected. It will be understood that the trigger sleeve 22 may alternatively be grasped between the thumb and fingers, for example, to position the device 10 for making an injection, and then effecting forward movement of the trigger sleeve 22 to effect this injection.

However, as was pointed out above in connection to the comparison of FIGS. 1 and 2, the device 10 is first placed by a user into its "inject" configuration before a jet injection can be effected. This conversion of the device 10 from its "storage" configuration to its inject configuration is effected by relative rotation of the body portions 12b and 12c, as is indicated by the arrow on FIG. 1. As is seen in FIG. 2, this relative rotation of the body portions 12b and 12c brings the projection 24 into engagement with blocking pin 26 and into alignment with recess 28, so that the trigger sleeve 22 is movable in the axial direction toward body portion 12b. However, viewing FIG. 4, it is seen that this relative rotation of the body portions 12b and 12c also threads body portion 12c by substantially one thread pitch dimension into the body portion 12b.

Because the body portion 12c and wall member 72 are abutting injection piston member 50, this piston member 50 is moved rightwardly, viewing FIG. 4, by substantially one thread pitch dimension. Consequently, the ram portion 60e of the injection piston 60 moves forward and forces piston member 50 forwardly by a sufficient amount that plug member 44 is dislodged hydraulically (recalling that the liquid medication in chamber 52 is substantially incompressible) from the outlet orifice 36b and into plug-capture chamber 46. In this chamber 46, the plug member 44 is retained an rests upon the ribs 48 while these rib provide a flow path leading (indicated by arrow 20a in FIG. 5) around the plug member 44 from the outlet orifice 36b to the injection orifice 18.

Although the conversion of device 10 from its "storage" configuration to its "inject" configuration unseals the injection cartridge 14, this is not detrimental to the integrity of the medication in chamber 52 because it happens mere moments before the device 10 is used to inject the medication into a patient. This injection is effected by placement of the device 10 with its surface 16 against the skin at the intended location of injection, and sliding of trigger sleeve 22 forward (which also assists in seeing that the device 10 is held firmly to the skin), so that the trigger block 102 slides along slot 100 to dislodge the dowel pin 88 from sear pin 94, viewing FIG. 5.

As is seen in FIG. 5, the result is that the hammer member 84 is driven forward by spring 92, impacts the capsule 82, and impales this capsule at penetrable wall 82d, as is seen in FIG. 5. The result is the penetrator spike 80 penetrates the wall 82c of the capsule 82, and allows pressurized gas from this capsule to flow along the bores 80a and 74 into the chamber 60d. This pressurized gas in chamber 60d drives piston member 60 forwardly, so that the piston member 50 in bore 36a is also driven forwardly. Forward movement of piston member 50 drives the liquid medication out of chamber 52, past the plug member 44 in plug-capture chamber 46, and out of injection orifice 18, forming injection jet 20.

After the jet injection depicted in FIG. 5, the device 10 is disposed of by the user of the device, and it is not again used. That is, the device 10 is a single-use device and is not designed or intended to be recharged or refilled. This design of the device 10 insures safety for those receiving an injection by use of the device 10 because they can be sure that only a new and never before used device is used to give them the injection. Further, the device 10 provides for long-term storage of the device and its pre-filled medication, so that devices 10 may be stockpiled in anticipation of such events as mass inoculations. The device 10 may be used under exigent circumstances as well, since it requires only a few seconds or less to convert it from its "storage" configuration to its "inject" configuration, after which the jet injection is immediately effected.

FIG. 6 provides a fragmentary view of an alternative embodiment of the jet injection device according to this invention. In FIG. 6, only the aft or trigger assembly end of the device is illustrated. The forward end of the device and its pre-filled medication injection cartridge may be substantially as depicted and described above. Because the device illustrated in FIGS. 6–8 has many features that are the same as, or which are analogous in structure or function to those illustrated and described above, these features are indicated on FIGS. 6–8 using the same reference numeral used above, and increased by one-hundred (100).

Viewing FIGS. 6–8 in conjunction with one another, it is seen that the injection device 110 includes a body portion 112c, which is necked to a slightly smaller diameter aft portion at 214. This aft portion defines a plurality of circumferential barbs 214a, and an end cap 202 is received on these barbs and is permanently engaged there by a matching set of inwardly extending barbs 202a. Slidably received in this body portion 112c is a one-piece molded hammer-and-sear member 184.

Preferably, this member 184 is molded of plastic polymer. The hammer-and-sear member 184 is seen in perspective in FIGS. 7 and 8. It is seen that this hammer-and-sear member 184 includes a cylindrical and tubular skirt section 216 defining a spring recess 216a, into which the spring 192 is captively received and preloaded to make the device 110 ready for use. A center wall portion 218 of the member 184 provides a surface 218a, which is engageable with the gas capsule 182 to move this capsule forward, and to impale the capsule on the penetrator spike (not seen in FIG. 6, but recalling FIGS. 3–5 above). In order to hold the hammer-and-sear member against the pre-load of spring 192, and to resist the pressure of this spring over a long term the member 184 includes three axially extending legs 220.

Each of these legs 220 is a portion of a cone-shaped section 220a, best seen in FIGS. 7 and 8. The transition between the circular cylindrical section 216, and the cone-shaped section 220a is indicated with a dashed line circumscribing the member 184 in FIG. 7. Forwardly of this transition, the legs 220 flare out by their own resilience. As is seen in FIG. 6, these legs 220, at an end surface 220b of each one engage upon a ring-like abutment member or rear ring member 222 carried within the body portion 112c. As is best appreciated by consideration of FIG. 7, it is seen that the end surfaces 220b of the legs 220 are not formed on the radius of the cone-shape at this end of the member 184 (i.e., at the cone diameter having a center line indicated as "CL" on FIG. 7), but are formed at a smaller radius corresponding generally with the circular diameter of the section 216 (indicated by the radius lines and character "R" of FIG. 7). During storage of the device 110, these end surfaces 220b rest upon the abutment member 222 and transfer the spring force from spring 192 to this abutment member on a long-term basis.

In order to prevent creep of the plastic polymer material from which the member 184 is formed, the surfaces 220b define cooperatively, a contact area which corresponds substantially to that of the diameter 216 of the member 184 multiplied by the radial thickness of the legs 220. This contact surface area is sufficient to prevent creeping of the polymer from which the member 184 is formed.

In order to effect release of the hammer-and-sear member 184 when it is desired to effect a jet injection with the device 110, the body portion 112c defines three axially extending slots 200 (only one of which is seen in FIG. 6), each corresponding to a respective one of the legs 220. As is seen in FIG. 6, the trigger sleeve 122 carries three trigger blocks 122a (again, only one of which is seen in FIG. 6) which are slidably received in the slots 200. When this trigger sleeve 122 is moved forward, the trigger blocks 122a simultaneously force respective ones of the legs 220 radially inwardly and out of engagement with the abutment member 222, overcoming both the inherent resilience of these legs and the component of spring force resulting from the radial flaring of these legs. It will be appreciated that in view of this combination of inherent resilience and outward flare of the legs 220, there is virtually no risk that the device 110 will trigger except in response to deliberate forward movement of the trigger sleeve 122.

Because the legs 220 are formed at a circular (rather than conical) radius, they nest together and are received into the ring-like abutment member 222. Thus, the spring 192 forces the hammer-and-sear member 184 forcefully forward, effecting a jet injection from device 110, as was explained above.

While the invention has been depicted and described by reference to two particularly preferred embodiments of the invention, such reference does not imply a limitation on the invention, and no such limitation is to be inferred. The invention is capable of considerable variation and alteration in its embodiments without departing from the scope of this invention. Accordingly, the invention is intended to be limited only by the spirit and scope of the appended claims, giving cognizance to equivalents in all respects.

I claim:

1. A needle-less hypodermic jet injection device comprising:
   a pre-filled drug injection cartridge including:
      a medication cylinder having an outlet orifice,
      an injection nozzle,
      a flow path communicating the outlet orifice to said injection nozzle,
      a drug-injection piston in a first position cooperating with said medication cylinder to define a variable-volume chamber of first selected size,
      a dose of substantially incompressible liquid medication substantially filling said variable-volume chamber at said first size with substantially no ullage volume,
      said drug-injection piston having a second position cooperating with said medication cylinder to define a variable-volume chamber of second selected size smaller than said first selected size;
   a hand piece assembly having a body holding said drug injection cartridge, said hand piece assembly including a source of pressurized gas, and means for selectively applying force from said pressurized gas to said drug injection piston to move said drug injection piston from said second position to a third position substantially ejecting said dose of liquid medication via said injection nozzle;
   said hand piece assembly including a first body portion holding said drug injection cartridge, and a second body portion manually movable relative to said first body portion, said second body portion including an abutment member selectively movable into engagement with said drug injection piston in response to manual relative movement of said first and second body portions to move said drug injection piston from said first position to said second position.

2. The device of claim 1, wherein said hand piece assembly further includes a first bore within said first body portion, a gas power piston movably received in said bore and having a ram portion extending into said drug injection cartridge to abut with said drug-injection piston, said body and gas-power piston cooperating to define a first variable-volume gas-power chamber in said first bore;
   said hand piece assembly further including a second body portion adjustably engaging with said first body portion, said second body portion defining an elongate second bore in gas flow communication with said first bore gas-power chamber and separated therefrom by a wall portion carried by said second body portion.

3. The device of claim 2 wherein said first body portion and said second body portion are threadably and adjustably engaged with one another, said second body portion carrying said abutment member.

4. The device of claim 3 wherein said wall portion includes said abutment member.

5. The device of claim 2 wherein said second body portion in said second bore further carries a cylindrical gas capsule, said cylindrical gas capsule providing said source of pressurized gas.

6. The device of claim 5 wherein said hand piece assembly second body portion is cylindrical, and a tubular trigger sleeve is movably carried by said second body portion to effect opening of said gas capsule.

7. A needle-less hypodermic jet injection device comprising:
   a pre-filled drug injection cartridge including: a medication cylinder having an outlet orifice, a plug member in a first position sealingly closing the outlet orifice, an injection nozzle, a flow path communicating the outlet orifice to said injection nozzle and providing a chamber for capturing said plug member in a second position, a drug-injection piston in a first position cooperating with said medication cylinder to define a variable-volume chamber of first selected size, a dose of substantially incompressible liquid medication substantially filling said variable-volume chamber at said first size with substantially no ullage volume, said drug-injection piston having a second position cooperating with said medication cylinder to define a variable-volume chamber of second selected size sufficiently smaller than said first selected size that said plug member is hydraulically forced from said first position at said outlet orifice and to a second position in said chamber;
   a hand piece assembly having a two-piece body having a first body portion holding said drug injection cartridge, and a second body portion providing an abutment movable relative to said first body portion to move said drug injection piston between said first and second positions;
   a source of pressurized gas including a hermetically sealed metallic gas capsule;
   trigger means for selectively penetrating said gas capsule and for applying force from said pressurized gas to said drug injection piston to move said drug injection piston from said second position to a third position substantially ejecting said dose of liquid medication via said injection nozzle.

8. The device of claim 7, wherein said first body portion defines a first bore, a gas-power piston movably received in said first bore, said gas-power piston having a piston head and a ram portion extending into said drug injection cartridge to abut with said drug-injection piston, said first body portion and said gas-power piston cooperating to define a first variable-volume gas-power chamber in said first bore;
   said second body portion sealingly and movably engaging with said first body portion to bound said gas-power chamber, said second body portion defining an elongate second bore in gas flow communication with said gas-power chamber, and said gas capsule being received into said second bore.

9. The device of claim 8 wherein said first body portion and said second body portion are threadably and adjustably engaged with one another, said second body portion including said abutment on a wall portion separating said second bore from said gas-power chamber.

10. A jet injection device comprising:
    a drug cartridge having a cylinder in which is movable a piston to cooperatively define a variable-volume chamber for holding a dose of liquid medication;
    a fine-dimension injection orifice in liquid flow communication with the variable-volume chamber to receive the liquid medication and discharge this medication as a high velocity forceful jet for hypodermic jet injection of the medication upon forceful movement of said piston in said cylinder;
    a power source for forcefully moving said piston in said cylinder in response to triggering of said injection device, and
    a trigger assembly for initiating forceful movement of said piston, said trigger assembly including a hammer member having a plurality of legs each having an end surface, a sear ring member upon which said end surfaces of said legs rests in a first position of the hammer member, means for urging said hammer member to a second position, and a trigger sleeve surrounding said hammer member and having a respective plurality of contact portions each engaging one of the plurality of legs to move said legs out of engagement with said sear ring upon axial movement of said trigger member.

11. The injection device of claim 10 wherein said hammer member includes a central wall portion from which extends in one axial direction a skirt defining a spring seat, said power source including a spring received into said skirt and into engagement with said central wall portion, said multitude of legs extending axially from said central wall portion in an opposite axial direction.

12. The injection device of claim 11 wherein said hammer member is a unitary molding of plastic polymer.

13. The injection device of claim 10 wherein said hammer member includes a first circular cylindrical portion and a second conically flaring portion axially arranged with one another.

14. The injection device of claim 13 wherein said first circularly cylindrical portion extends in one direction from said central wall portion, and said plurality of legs cooperatively define said second conically flaring portion and extend axially in said opposite axial direction from said central wall portion.

15. The injection device of claim 14 wherein said conically flaring portion has a conical diameter at an end of said hammer member, said plurality of legs are each part-circular segments having circular radii which are substantially equal to the radius of the circular cylindrical portion, whereby, said sear ring has an inner diameter substantially equal to said circular cylindrical portion of said hammer member and said plurality of legs in a second position are nested circumferentially adjacent to one another within said sear ring member.

16. A unitary elongate molded plastic polymer hammer member, said hammer member comprising:
   a central wall portion extending radially;
   a circular cylindrical portion extending axially in one direction from said central wall portion, said circular cylindrical portion including a tubular skirt and cooperating with said central wall portion to define a spring seat into which a spring may be received to engage upon said central wall portion;
   a conically flaring portion extending in an opposite axial direction from said central wall portion, said conical portion including a plurality of circumferentially spaced apart resilient legs each extending axially to terminate in a respective axial end surface engageable with a sear ring in a first position of the legs to support said hammer member in opposition to force from the spring exerted on said central wall portion, said legs in said first position cooperatively defining a conical diameter at said end surfaces, and said legs at said end surfaces each also defining a circular radius which are substantially equal to the radius of said circular cylindrical portion;
   whereby, said plurality of legs are movable to a second position in opposition to said resilience of said legs, in said second position said plurality of legs being circumferentially nested adjacent to one another and cooperatively defining a diameter substantially equal to that of said cylindrical portion.

17. A method of operating a needle-less hypodermic jet injection device using an injection cartridge having a cylinder receiving liquid medication, an orifice for forming the liquid into a high-velocity hypodermic injection jet, a plug member in a first position sealingly separating said medication from said orifice, and said plug member in a captive second position allowing communication of medication to said orifice, and an injection piston movable sealingly in said cylinder to displace said liquid medication via said orifice; said method including steps of:
   providing said device with a two-piece body having a first body portion defining a first bore into which is received a gas-power piston, and a second body portion defining a second bore into which is sealingly and movably received a hermetically sealed pressurized gas capsule; utilizing said first and second body portions and said gas-power piston to cooperatively define a variable-volume chamber; and
   first relatively moving said first and second body portions to forcefully move said plug member from said first position to said captive second position to unseal said injection cartridge, and then
   utilizing communication of pressurized gas from said pressurized gas capsule into said variable-volume chamber to forcefully move said gas-power piston to displace said liquid medication from said cartridge via said orifice to effect a hypodermic jet injection.

18. The method of operating a needle-less injection device of claim 17 further including the step of utilizing a unitary molded plastic polymer hammer member to drive said gas capsule upon an impaling spike communicating pressurized gas to said variable-volume chamber.

19. A method of operating a needle-less hypodermic jet injection device using an injection cartridge having a cylinder receiving liquid medication, an orifice for forming the liquid into a high-velocity hypodermic injection jet, a plug member sealingly separating said medication from said orifice, and an injection piston movable sealingly in said cylinder to displace said liquid medication via said orifice; said method including steps of:
   providing said device with a two-piece body having a first body portion defining a first bore into which is received a gas-power piston, and a second body portion defining a second bore into which is sealingly and movably received a hermetically sealed pressurized gas capsule; utilizing said first and second body portions and said gas-power piston to cooperatively define a variable-volume chamber; and
   first relatively moving said first and second body portions to forcefully move said plug member to unseal said injection cartridge, and then
   utilizing communication of pressurized gas from said pressurized gas capsule into said variable-volume chamber to forcefully move said gas-power piston to displace said liquid medication from said cartridge via said orifice to effect a hypodermic jet injection;
   further including the step of providing said molded unitary plastic polymer hammer member with a plurality of axially extending legs each having an end surface engaging upon a sear ring surface to support said hammer member, and simultaneously slipping said plurality of legs off of said sear ring surface radially inwardly to be received in circumferentially adjacent nested position within said sear ring surface to allow axial movement of said hammer member.

20. A needle-free hypodermic jet injection device comprising:
   a body substantially formed of plastic polymer;

a jet injection cartridge carried by said body and including a cylinder and piston cooperatively defining a variable-volume chamber receiving a dose of liquid medication, and a fine-dimension jet injection orifice in liquid flow communication with said variable volume chamber;

a metallic pre-filled hermetically-sealed single-use gas pressure cartridge axially movably disposed in said body, said gas pressure cartridge having a penetrable wall portion and said body including a penetrator axially spaced from and confronting said penetrable wall portion for penetrating said penetrable wall portion of said gas cartridge and releasing pressurized gas from said cartridge;

said device further including means responsive to pressurized gas released from said gas pressure cartridge for applying force to said liquid medication to eject said medication via said jet injection orifice;

said device further including means for selectively moving said gas pressure cartridge axially and impaling said gas pressure cartridge at said penetrable wall portion upon said penetrator in response to a singular user input so as to release pressurized gas from said gas pressure cartridge and to eject said medication via said jet injection orifice to effect a hypodermic jet injection.

* * * * *